United States Patent
Altman et al.

(10) Patent No.: US 8,988,214 B2
(45) Date of Patent: Mar. 24, 2015

(54) SYSTEM, METHOD, APPARATUS, OR COMPUTER PROGRAM PRODUCT FOR EXERCISE AND PERSONAL SECURITY

(75) Inventors: Steven R. Altman, La Jolla, CA (US); David Vigil, Rancho Santa Fe, CA (US); Thomas F. Doyle, San Diego, CA (US); David J. Ross, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 547 days.

(21) Appl. No.: 13/315,106

(22) Filed: Dec. 8, 2011

(65) Prior Publication Data

US 2012/0150327 A1 Jun. 14, 2012

Related U.S. Application Data

(60) Provisional application No. 61/422,075, filed on Dec. 10, 2010.

(51) Int. Cl.
*G08B 21/00* (2006.01)
*G06F 19/00* (2011.01)
(Continued)

(52) U.S. Cl.
CPC ..... *G06F 19/3418* (2013.01); *A61B 2560/0295* (2013.01); *A61B 5/1118* (2013.01); *A61B 5/0816* (2013.01); *A61B 2562/0219* (2013.01);
(Continued)

(58) Field of Classification Search
CPC .............................. G06F 19/3418; G01S 19/19
USPC ............... 340/539.1, 539.12, 539.13, 539.15, 340/539.2, 539.21, 573.1, 573.4; 600/300, 600/301
See application file for complete search history.

(56) References Cited

U.S. PATENT DOCUMENTS

| 6,847,295 | B1 | 1/2005 | Taliaferro et al. |
| 7,534,206 | B1 | 5/2009 | Lovitt et al. |

(Continued)

FOREIGN PATENT DOCUMENTS

| EP | 0846440 A2 | 6/1998 |
| EP | 2042081 A1 | 4/2009 |

(Continued)

OTHER PUBLICATIONS

Website "Actively Mobile: Mobile Design for Running," product brochure, Jennifer L. Bove (j.bove@interaction-ivrea.it), Interaction Design Institute Ivrea, May 2005, Website: http://www.activelymobile.com/jbove_thesis_web.pdf, Date Accessed: Aug. 24, 2010.

(Continued)

*Primary Examiner* — Jeffery Hofsass
(74) *Attorney, Agent, or Firm* — Howard Seo

(57) ABSTRACT

A method and system for tracking exercise and personal security includes providing hardware for a portable computing device that allows the device to be worn on a person. The method includes receiving a selection of an exercise option with the portable computing device and receiving a selection of an automated alert option for personal security with the portable computing device while a person trains or competes. The portable computing device that is worn may display one or more biological outputs on a display and it may provide a user interface which has one or more selectable instant alert options. The user interface may also support two-way audio communications.

41 Claims, 8 Drawing Sheets

(51) Int. Cl.
*A61B 5/00* (2006.01)
*G01S 19/19* (2010.01)
*G01S 19/17* (2010.01)
*A61B 5/11* (2006.01)
*A61B 5/08* (2006.01)
*A61B 5/021* (2006.01)
*A61B 5/145* (2006.01)
*A61B 5/0205* (2006.01)
*A61B 5/024* (2006.01)

(52) U.S. Cl.
CPC ............... *A61B5/1112* (2013.01); *A61B 5/021* (2013.01); *A61B 5/0022* (2013.01); *A61B 5/14517* (2013.01); *G01S 19/19* (2013.01); *A61B 2562/0261* (2013.01); *A61B 5/0205* (2013.01); *A61B 5/14532* (2013.01); *A61B 2505/09* (2013.01); *A61B 5/02438* (2013.01); *G01S 19/17* (2013.01); *A61B 5/02405* (2013.01); *A61B 5/747* (2013.01); *A61B 5/11* (2013.01); *G06F 19/3481* (2013.01)
USPC ............. 340/539.11; 340/539.12; 340/573.1; 600/301

(56) References Cited

U.S. PATENT DOCUMENTS

2003/0218539 A1* 11/2003 Hight ....................... 340/539.13
2007/0260482 A1 11/2007 Nurmela et al.
2008/0051667 A1 2/2008 Goldreich
2009/0295596 A1 12/2009 Downey et al.

FOREIGN PATENT DOCUMENTS

| | | |
|---|---|---|
| JP | H10295652 A | 11/1998 |
| JP | H11128396 A | 5/1999 |
| JP | H11206721 A | 8/1999 |
| JP | 2007292505 A | 11/2007 |
| JP | 2008503268 A | 2/2008 |
| JP | 2010218126 A | 9/2010 |
| JP | 2010232963 A | 10/2010 |
| KR | 20070048168 A | 5/2007 |
| WO | WO-02067449 A2 | 8/2002 |
| WO | WO-2004015606 A1 | 2/2004 |
| WO | WO-2005041131 A2 | 5/2005 |
| WO | WO-2006009830 A2 | 1/2006 |
| WO | WO-2007033194 A2 | 3/2007 |
| WO | WO-2008030484 A2 | 3/2008 |

OTHER PUBLICATIONS

Website "http://www.strava.com/tour—Cycling Training Log—Chart, Log, and Categorize Climbs and Rides | Strava Tour," Website: http://www.strava.com/tour, Date Accessed: Sep. 30, 2010.
International Search Report and Written Opinion—PCT/US2011/064317—ISA/EPO—Sep. 21, 2012.

* cited by examiner

SYSTEM, METHOD, APPARATUS, OR COMPUTER PROGRAM PRODUCT FOR EXERCISE AND PERSONAL SECURITY

PRIORITY CLAIM AND CROSS-REFERENCE TO RELATED APPLICATIONS

The application claims priority under 35 U.S.C. §119(e) to U.S. Provisional Patent Application Ser. No. 61/422,075, entitled, "System, method, apparatus, or computer program product for exercise and personal security," filed on Dec. 10, 2011, the entire contents of which are hereby incorporated by reference.

DESCRIPTION OF THE RELATED ART

Currently, there are a number of different types of devices available for monitoring human subjects while they exercise. Specifically, some of these devices may allow for the monitoring of at least one of heart rate, breathing rate, body temperature, oxygen level in the blood, and blood pressure, just to name a few physiological conditions that may be monitored with these devices.

Often, these devices may be bulky in size and may not be conducive for casual wearing by a human subject. Another problem with these conventional devices is that they are typically tailored for a specific function and do not provide multiple functions such as monitoring multiple physiological conditions listed above with a single device.

Another problem faced by athletes and people who exercise is the integration of exercise monitoring and communication. Specifically, many exercise monitoring devices do not support two-way communications such as two-way radio frequency transmissions (like those used for cellular telephone calls). Often, athletes and people who exercise need to carry or wear an exercise monitoring device in addition to carrying a portable communications device like a mobile phone.

Another problem faced by athletes and people who exercise is personal security. For example, many female athletes and females who exercise must be very vigilant when they are training in remote areas or in locations in which personal security may be at risk. Female athletes and females who exercise in remote areas are generally susceptible to assaults or attacks by male assailants.

To mitigate risk of an attack or an assault, female athletes and females who exercise often train/exercise with a companion if that training or exercise requires the female athlete or the female exerciser to move across geographical regions in which personal security may be at risk. In other instances, female athletes and females who exercise must inform others of their progress or starting/stopping points during their training so that others will know that the female athlete/exerciser is not in any danger with respect to personal security.

Accordingly, what is needed is a system and method that may overcome the problems associated with single function exercise monitoring devices. Specifically, a system and method is needed for providing an exercise monitoring device that supports two-way communications and which may integrate personal security functions that may be tracked by a remote computer server.

SUMMARY

A method and system for tracking exercise and personal security includes providing hardware for a portable computing device that allows the device to be worn on a person. The method includes receiving a selection of an exercise option with the portable computing device and receiving a selection of an automated alert option for personal security with the portable computing device while a person trains or competes. The portable computing device that is worn may display one or more biological outputs on a display and it may provide a user interface which has one or more selectable instant alert options. The user interface may also support two-way audio communications.

BRIEF DESCRIPTION OF THE DRAWINGS

In the figures, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures.

DETAILED DESCRIPTION

The word "exemplary" is used herein to mean "serving as an example, instance, or illustration." Any aspect described herein as "exemplary" is not necessarily to be construed as preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

The term "content" may also include files having executable content, such as: object code, scripts, byte code, markup language files, and patches. In addition, "content" referred to herein, may also include files that are not executable in nature, such as documents that may need to be opened or other data files that need to be accessed.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

In this description, the terms "communication device," "wireless device," "wireless telephone," "wireless communication device," "wireless handset," and "smartphone," are used interchangeably. With the advent of third generation ("3G") and fourth generation ("4G") wireless technology, greater bandwidth availability has enabled more portable computing devices with a greater variety of wireless capabilities. Therefore, a wearable wireless portable device may comprise a cellular telephone, a pager, a PDA, a smartphone, a navigation device, or a hand-held computer with a wireless connection or link.

Figure 1A:
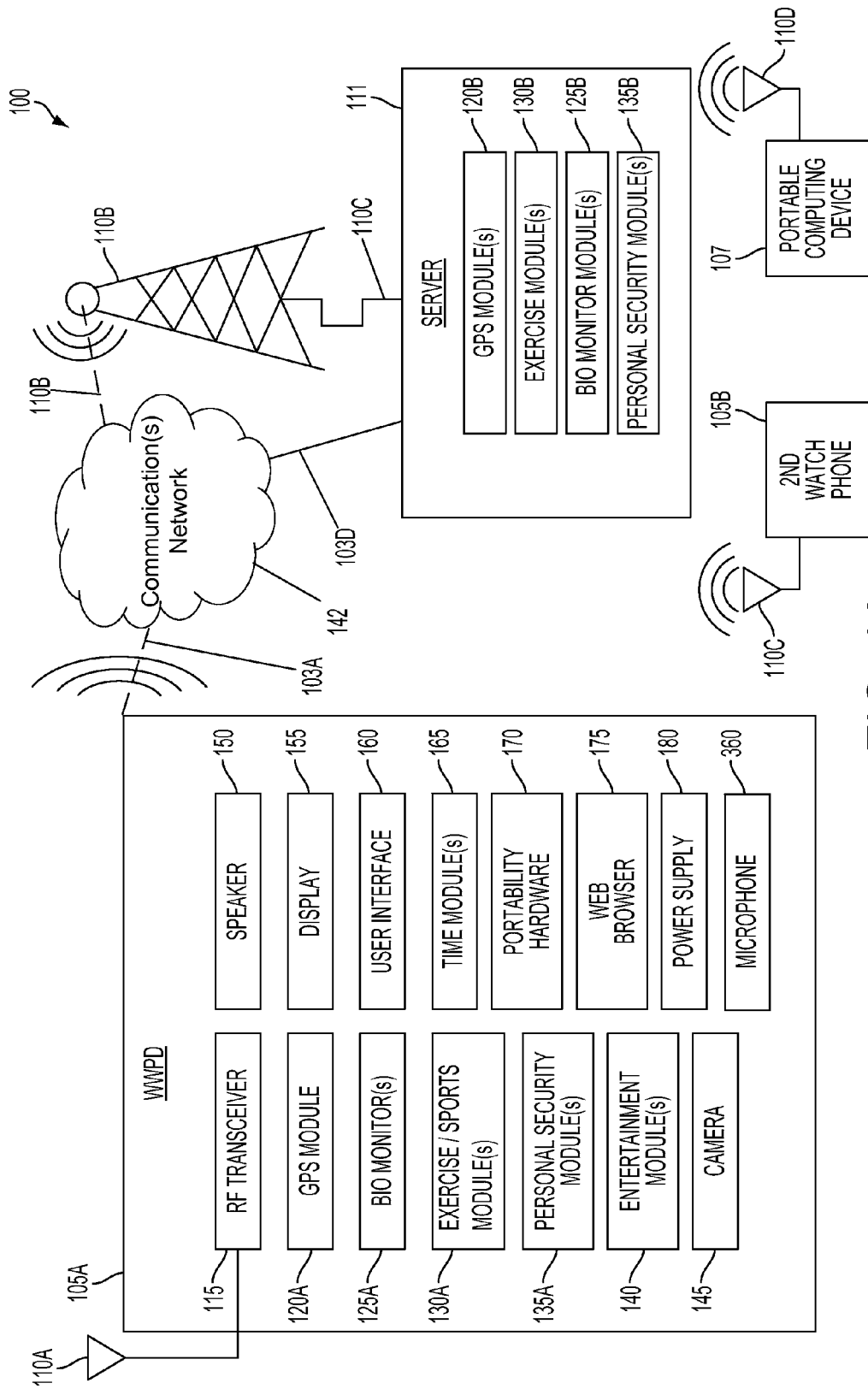
FIG. 1A is a system wide functional block diagram of a wearable wireless portable device coupled to a wireless communications network.

FIG. 1A is a system wide functional block diagram of a wearable wireless portable device 105A coupled to a wireless communications network 142. Many of the system elements illustrated in FIG. 1A are coupled via communications links 103 to the communications network 142.

The links 103 illustrated in FIG. 1 may comprise wired or wireless links. Wireless links include, but are not limited to, radio-frequency ("RF") links, infrared links, acoustic links, and other wireless mediums. The communications network 142 may comprise a wide area network ("WAN"), a local area network ("LAN"), the Internet, a Public Switched Telephony Network ("PSTN"), a paging network, or a combination thereof. The communications network 142 may be established by broadcast RF transceiver towers 110B. However, one of ordinary skill in the art recognizes that other types of communication devices besides broadcast RF transceiver towers 110B are included within the scope of the invention for establishing the communications network 142. The wearable wireless portable device ("WWPD") 105A is shown to have an antenna 110A so that a respective wearable wireless portable device 105A may establish wireless communication links 103 with the communications network 142 via RF transceiver towers 110B.

Figure 1B:
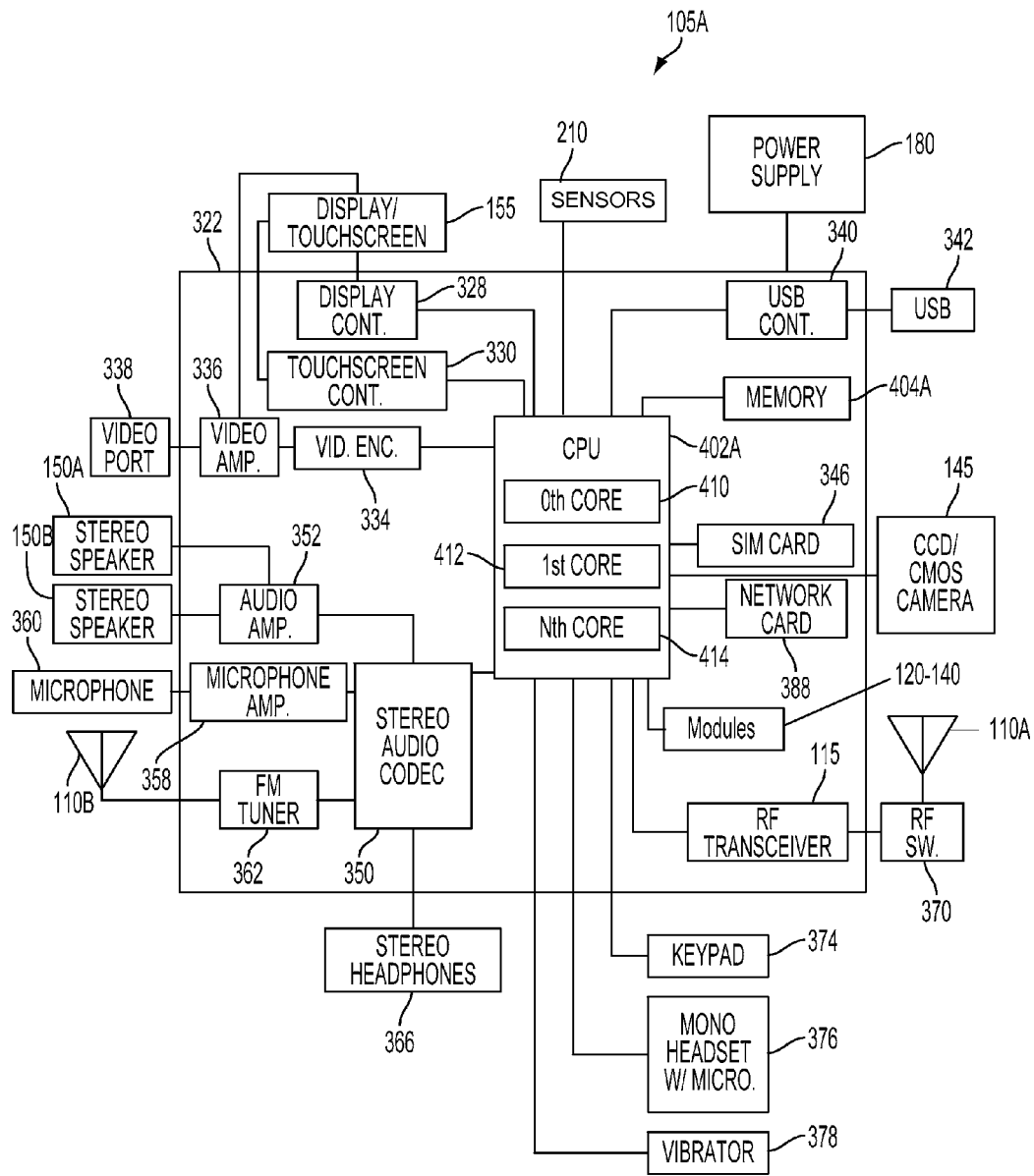
FIG. 1B is a detailed functional block diagram of a second aspect of a wearable wireless portable device.

The wearable wireless portable device 105A may comprise a plurality of various software and/or hardware elements. Such software and/or hardware elements include, but are not limited to, a radio-frequency ("RF") transceiver 115, a global positioning satellite (GPS) module 120A, biological or physiological monitor(s) 125A, an exercise module 130A, a personal security module 135A, and entertainment module 140, a camera 145, a speaker 150, a display 155, a user interface 160, a time module 165, portability hardware 170, a web browser module 175, a power supply 180, and microphone 360. The wearable wireless portable device 105A may comprise a central processing unit ("CPU") 402A as illustrated in FIG. 1B described below. The CPU 402A may execute the functions described above or it may have several dedicated circuits that provide the functions described above.

The RF transceiver 115 may be coupled to the antenna 110A. The RF transceiver 115 may support one or more multiple RF communication types. For example, the RF transceiver 115 may support cellular phone type RF communications. Other communication types include, but are not limited to, fixed wireless, portable communication systems ("PCS"), or satellite communications systems. The RF transceiver 115 may provide for multiple access communications, in accordance with any standard or protocol, such as, for example, code division multiple access ("CDMA"), time division multiple access ("TDMA"), frequency division multiple access ("FDMA"), or Global System for Mobile communications ("GSM"), or any combination thereof.

The RF transceiver 115 in combination with the network 142 may also support QChat® service type instantaneous communications. QChat® is a software application developed by Qualcomm Internet Services (QIS), a division of Qualcomm, Inc. and part of the Qualcomm Wireless and Internet group. QChat® provides a reliable method of instant connection and two-way communication between users who may be in different and who are operating within the same type of network architecture. QChat® may comprise a software application developed for the Binary Runtime Environment for Wireless ("BREW") platform.

"Press-to-Transmit" ("PTT") is a method of conversing on half-duplex communication lines for 3G and 4G networks. QChat® handsets and server software as of this writing allow users of the wearable wireless portable device 105A to connect instantaneously with other QChat® users anywhere in the world with the push of a button. In addition, the QChat® service enables one-to-one (private) and one-to-many (group) calls over the 3G and 4G networks.

As understood by one of ordinary skill in the art, QChat® may use standard Voice over Internet Protocol (VoIP) technologies. Voice information may be sent in digital form over internet protocol ("IP") data networks in discrete packets rather than traditional circuit-switched protocols such those used in the public switched telephone network ("PSTN").

The RF transceiver 115 may also support simple messaging system (SMS) functions such as texting. The RF transceiver 115 may allow the operator of the wearable wireless portable device 105A to forward inbound or incoming phone calls to a text to speech engine that may comprise software and/or hardware which are part of the user interface module 160. Alternatively, the text to speech engine hardware and/or software may be part of the server 111 which may receive phone calls that are forwarded to it by the wearable wireless portable device 105A.

The GPS module 120A may comprise hardware and/or software that supports the United States Global Positioning System ("GPS"). However, other global navigation satellite systems ("GNSS") are included within the scope of the invention and may be supported by hardware and/or software executed by the wearable wireless portable device 105A. Other GNSS or Satellite Positioning Systems ("SPS") include, but are not limited to, the Russian GLONASS system, and the European Galileo System. The GPS module 120A may provide an operator of the wearable wireless portable device 105A with a current set of the geographical coordinates for the location of the device 105A. The wearable wireless portable device 105A may also provide maps showing the geographical coordinates on the display 155. The GPS module 120A may also transmit its calculated geographical coordinates using the RF transceiver 115 over the network 142 to a remote server 111, a second wearable wireless portable device 105B, and/or a portable computing device 107.

The wearable wireless portable device 105A may include one or more biological or physiological monitors 125A. These monitors 125A may check and track one or more physiological parameters. Exemplary measured physiological and/or calculated parameters include, but are not limited to: heart rate, calories burned, variability in heart rate, breathing rate, arrhythmia of the heart (if any), general rhythm and functioning of the heart, blood pressure, abnormal body movements (convulsions), body position, general body movements, body temperature, presence and quantity of sweat, oxygenation, and glucose levels in the blood. The monitors 125A may work in concert or in conjunction with one or more sensors 210 as described in FIG. 2 discussed below. Such sensors 210 may include, but are not limited to, heart rate sensors, blood pressure sensors, strain gauges, gyroscopes, accelerometers, pedometers, thermometers, thermocouples, glucometers, and other similar sensors as understood by one of ordinary skill in the art.

Figure 2:
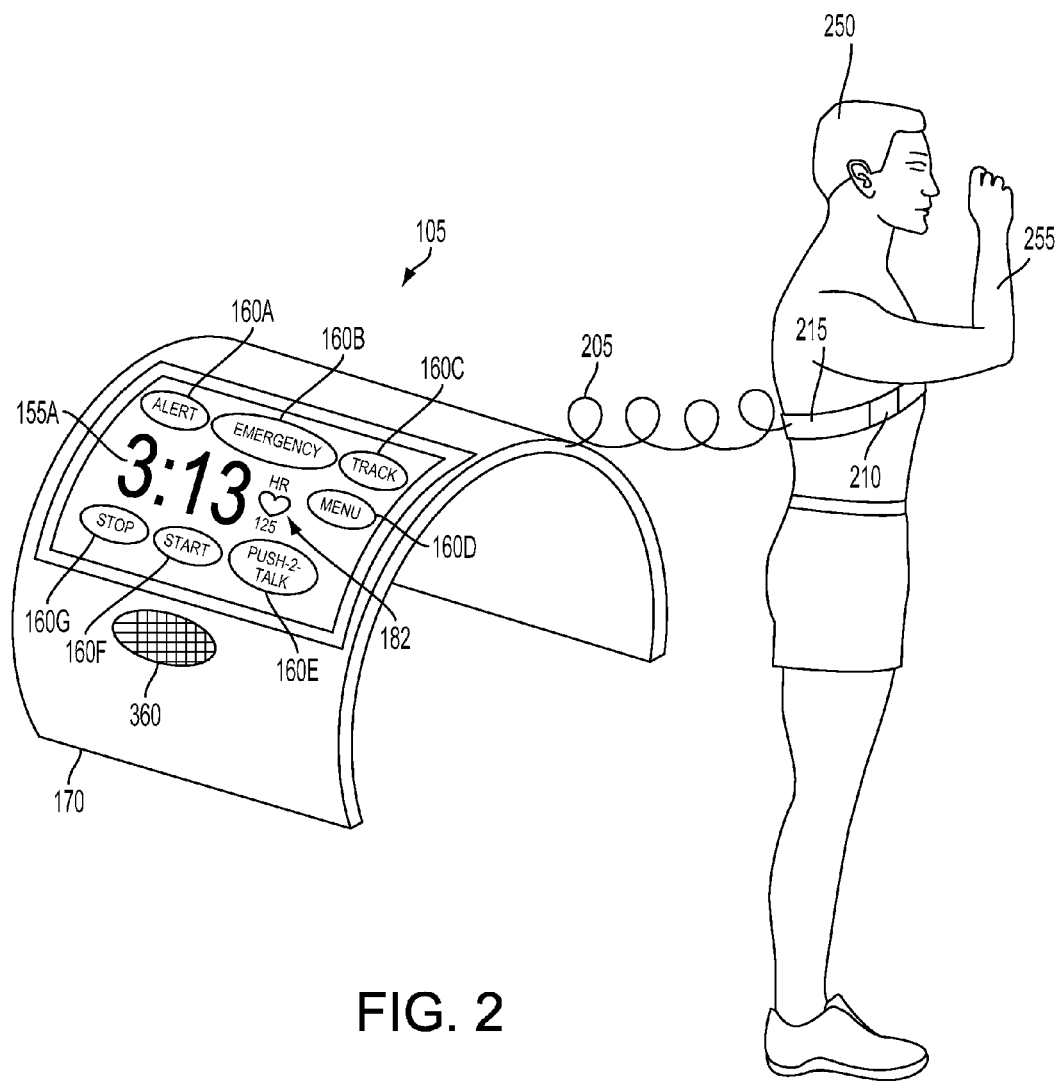
FIG. 2 is a diagram of a exemplary wearable wireless portable device having anatomical mounting hardware.

The monitors 125A and the sensors 210 of FIG. 2 may work in concert and/or in communication with one or more exercise or sports activity modules 130A. The exercise or sports activity modules 130A may be designed for specific physical activities that may include, but are not limited to, jogging, running, walking, bicycling, swimming, rowing, strength training, yoga, mountain biking, skiing, hiking, and mountain climbing. The system may track other similar physical activities that include all sports and sports related activities.

Each exercise or sports activity module 130A may be tailored for a specific physical activity. For example, a jogging sports activity module 130A may track the heart rate, calories burned, as well as the distance traveled by the operator of the wearable wireless portable device 105A. A swimming sports activity module 130A may also track and monitor heart rate, calories burned, water temperature, as well as the number of laps taken by the operator of the wearable wireless portable device 105A. The sports activity module 130A may also track and monitor time according to the activity selected by the wearable wireless portable device 105A.

In addition to tracking the exercise or sports activity of the operator of the wearable wireless portable device 105A, the exercise module 130A may also receive performance data that is transmitted to the wearable wireless portable device 105A from other wearable wireless portable devices 105B as illustrated in FIG. 1A. In one embodiment, the wearable wireless portable device 105A may receive data regarding other operators of other wearable wireless portable devices 105B that may be participating in the same exercise or sports activity of the operator of the wearable wireless portable device 105A. Such performance data may include, but is not limited to, (1) geographical locations of other athletes or exercisers that may be shown on display 155, and (2) specific metrics of other athletes and exercisers. The specific metrics may include, but are not limited to, calories burned, current speed, current exercise rate, or athletic rate, etc. Performance data may include data from famous athletes who have uploaded and stored their exercise or sports activity data. In this way, the wearable wireless portable device 105 may foster competition among multiple athletes and/or exercisers in which these people may be significantly geographically diverse (i.e., separate from one another), such as people comparing performance data to one another who live in different towns, cities, states, countries, etc.

The exercise module 130A may also track and monitor benchmarks associated with stored data such as benchmarks recorded and stored at a server 111 by famous or noteworthy athletes. In other words, the exercise module 130A may provide a continuous comparison of a current exercise or sports activity of the operator of the wearable wireless portable device 105A to stored results of a famous or noteworthy athlete who has uploaded and stored his or her exercise or sports activity data (also referred to as performance data throughout this document). Details about these comparative functions performed by the exercise module 130A will be described in further detail below in connection with FIG. 3 and FIG. 4.

The personal security module 135A may comprise hardware and/or software modules that allow the operator to select from a plurality of personal security features and functions. For example, the personal security module 135A may activate a function such that the position of the wearable wireless portable device 105A as monitored and detected by the GPS module 120A may be sent over the communications network 142. This data may be received by the server 111. In this way, a third-party may monitor movement of the wearable wireless portable device 105A which has activated the personal security personal security module 135A. The personal security module 135A may include user-defined functions such as an alert or an alarm button that may be depressed by the operator of the wearable wireless portable device 105A. The alert or alarm button may be depressed by the operator if he or she is experiencing a security issue, such as a robbery, kidnapping, assault, etc.

The personal security module 135A may also be programmed to provide periodic updates of the location of the wearable wireless portable device 105A as selected by the operator. The personal security module 135A may generate periodic text messages indicating that the status of the operator is good. Likewise, the personal security module 135A may also operate as a "kill switch." For this feature, the operator is required to push a button which transmits a message stating that the "operator is OK" according to certain time intervals and/or locations or both. When the operator of the wearable wireless portable device 105A does not push the button after a period of time and/or at a location or both, then an alarm signal may be triggered and generated by the wearable wireless portable device 105A. This alarm signal is communicated over the network 142 to the server 111. The alarm signal in an exemplary embodiment may take the form of a text message. The generation of text messages may consume very little or low bandwidth. The text message functions may operate like conventional wireless devices which utilize 3G and 4G wireless connections.

The personal security module 135A may support other types of security features and/or functions. Such other types of security features and/or functions may include an alert feature that allows the operator of the wearable wireless portable device 105A to send an alert status to the server 111. With this alert status, a remote operator such as a second wearable wireless portable device 105B or a portable computing device 107 may be notified to start tracking or monitoring the status of the first wearable wireless portable device 105A.

In other words, the personal security module 135A may support an alert feature that does not require immediate action with respect to a party monitoring the location of the wearable wireless portable device 105A. This alert feature may only require the party who has access to the server 111 to start focusing on the location and movement of the wearable wireless portable device 105A until the operator of the wearable wireless portable device 105A indicates that further monitoring by the third party is no longer needed.

The personal security module 135A may also support emergency functions and/or features such as a 911 emergency call feature. This means when the 911 emergency call feature is activated, the personal security module 135A may be programmed to send the current location of the wearable wireless portable device 105A along with a predetermined or canned message. The canned message may comprise a text message and/or a voice message that identifies the name of the operator of the wearable wireless portable device 105A along with instructions for emergency personnel/first responders to come to the rescue of the operator immediately. The personal security module 135A may also support specific emergency functions such as identifying the category or type of emergency and requesting emergency assistance corresponding to the category or type selected by the operator of the wearable wireless portable device 105A.

That is, the personal security module 135A may support an emergency medical function, an emergency police function, and an emergency fire function, or any combination thereof. In this way, the operator of the wearable wireless portable device 105A may select the type of emergency that may be experienced by the operator so that proper emergency personnel/first responders are appropriately notified and requested to arrive at the location of the wearable wireless portable device 105A.

As noted above, the wearable wireless portable device 105A may also comprise one or more entertainment modules 140. The one or more entertainment modules 140 may support functions and/or features or a combination thereof that include, but are not limited to, audio players, video players, video games, and other entertainment functions. For example, the entertainment module 140 may comprise an MP3 player for playing audio files that include music files.

The wearable wireless portable device 105A may also comprise a camera 145 that may support conventional photographs as well as video. Further details about the camera 145 will be described below in connection with FIG. 1B. The wearable wireless portable device 105A may also include a speaker 150, a microphone 360, a display 155, and a user interface module 160. The user interface module 160 may be coupled to both the speaker 150, the display 155, and the microphone 360.

The user interface module 160 may support or be part of an operating system ("OS") that is integrated with the graphics shown on a display 155 and which may support keyed-in commands as well as voice activated commands. The user interface module 160 may provide for a simulated keyboard on the display 155. Alternatively, a physical keyboard or keypad 374 such as illustrated in FIG. 1B may be part of the user interface module 160.

The wearable wireless portable device 105A may also comprise one or more time modules 165 that may be coupled to the display module 155, the speaker 150, and the exercise or sports activity modules 130A. The time modules 165 may track current time as well as times and other time zones throughout the world. The time modules 165 may be accessed and may provide data to the exercise or sports activity modules 130A such as, but not limited to, lap time, running or jogging rate, and other similar time features. The time modules 165 may be coupled to the display 155. The times tracked by the time modules 165 may be displayable to the operator of the wearable wireless portable device 105A.

The wearable wireless portable device 105A may also comprise portability hardware 170 which may take on various different forms. For example, the portability hardware 170 may comprise physical structures such as one or more bands coupled together so the wearable wireless portable device 105A is worn as a bracelet or like a watch. In other cases, the portability hardware 170 may comprise other bands, straps, or fasteners, so the wearable wireless portable device 105A may be worn on the other parts of the human anatomy. For example, the WWPD 105A may be worn on the arm of a person as well as around the torso of a person.

The wearable wireless portable device 105A may also comprise a web browser module 175 that is coupled to the display 155B, user interface module 160, and the RF transceiver 115. The web browser module 175 may allow the operator to access the Internet as well as allowing various modules such as the GPS module 120A and the exercise/sports activity modules 130A to upload or download particular information.

The wearable wireless portable device 105A may also include a power supply 180. The power supply 180 may include, but is not limited to, batteries, capacitors, solar cells, mechanical power generation devices (i.e. self winding equipment), and any combination thereof as well as similar power supplies 18 known to one of ordinary skill the art.

The server 111 may comprise one or more modules which mirror those which are contained within or part of the wearable wireless portable device 105A. That is, the server 111 may comprise one or more GPS modules 120B, one or more exercise modules 130B, one or more bio monitor modules 125B, and one or more personal security modules 135B. The modules of the server 111 may be complementary relative to the modules of the wearable wireless portable device 105A and may work in concert with the modules of the wearable wireless portable device 105A.

As noted previously, the server 111 may communicate with other wearable wireless portable devices 105B as well as other portable computing devices 107. Other portable computing devices 107 may include handheld computers, laptop computers, and desktop computers.

Referring to FIG. 1B, an exemplary, non-limiting aspect of a wearable wireless portable device 105A is shown. The wearable wireless portable device 105A includes an on-chip system 322 that includes a multicore CPU 402A. The multicore CPU 402A may include a zeroth core 410, a first core 412, and an Nth core 414. According to alternate exemplary embodiments, the CPU 402 may also comprise those of single core types and not one which has multiple cores.

As illustrated in FIG. 1B, a display controller 328 and a touch screen controller 330 are coupled to the multicore CPU 402A. In turn, the touch screen display 155 external to the on-chip system 322 is coupled to the display controller 328 and the touch screen controller 330.

FIG. 1B further shows that a video encoder 334, e.g., a phase alternating line (PAL) encoder, a sequential color a memoire (SECAM) encoder, or a national television system(s) committee (NTSC) encoder, is coupled to the multicore CPU 402A. Further, a video amplifier 336 is coupled to the video encoder 334 and the touch screen display 108. Also, a video port 338 is coupled to the video amplifier 336. As shown in FIG. 1B, a universal serial bus (USB) controller 340 is coupled to the multicore CPU 402A. Also, a USB port 342 is coupled to the USB controller 340. Memory 404A and a subscriber identity module (SIM) card 346 may also be coupled to the multicore CPU 402A.

Further, as shown in FIG. 1B, a digital camera 145 may be coupled to the multicore CPU 402A. In an exemplary aspect, the digital camera 145 is a charge-coupled device (CCD) camera or a complementary metal-oxide semiconductor (CMOS) camera.

As further illustrated in FIG. 1B, a stereo audio coder-decoder (CODEC) 350 may be coupled to the multicore CPU 402A. Moreover, an audio amplifier 352 may coupled to the stereo audio CODEC 350. In an exemplary aspect, a first stereo speaker 150A and a second stereo speaker 150B are coupled to the audio amplifier 352. FIG. 1B shows that a microphone amplifier 358 may be also coupled to the stereo audio CODEC 350. Additionally, a microphone 360 may be coupled to the microphone amplifier 358. In a particular aspect, a frequency modulation (FM) radio tuner 362 may be coupled to the stereo audio CODEC 350. Also, an FM antenna 110B is coupled to the FM radio tuner 362. Further, stereo headphones 366 may be coupled to the stereo audio CODEC 350.

FIG. 1B further illustrates that a radio frequency ("RF") transceiver 115 may be coupled to the multicore CPU 402A. An RF switch 370 may be coupled to the RF transceiver 368 and an RF antenna 110A. As shown in FIG. 1B, a keypad 374 may be coupled to the multicore CPU 402A. Also, a mono headset with a microphone 376 may be coupled to the multi-core CPU 402A. Further, a vibrator device 378 may be coupled to the multicore CPU 402A.

FIG. 1B also shows that the power supply 180 may be coupled to the on-chip system 322. According to one aspect, the power supply 180 is a direct current (DC) power supply that provides power to the various components of the wearable wireless portable device 105A that require power. Further, in a particular aspect, the power supply 180 is a rechargeable DC battery or a DC power supply that is derived from an alternating current (AC) to DC transformer that is connected to an AC power source.

FIG. 1B further illustrates a network card 388 that may be used to access a data network, e.g., a local area network, a personal area network, or any other network. The network card 388 may be a Bluetooth network card, a WiFi network card, a personal area network (PAN) card, a personal area network ultra-low-power technology (PeANUT) network card, or any other network card well known in the art. Further, the network card 388 may be incorporated into a chip, i.e., the network card 388 may be a full solution in a chip, and may not be a separate network card 388.

The multicore CPU 402A may be coupled to software and/or hardware embodiments of the modules 120, 125, 130, 135, and 140 (120-140) which are described above in connection with FIG. 1A. These modules 120-140 may take the form of software and/or hardware, such as, but not limited to an application integrated circuit (ASIC), and/or firmware. These modules 120-140 of FIG. 1A are generally responsible for providing the global positioning functions, bio monitoring functions, exercise/athletic performance tracking functions, personal security functions, and entertainment functions as described above in connection with FIG. 1A.

As depicted in FIG. 1B, the touch screen display 155, the video port 338, the USB port 342, the camera 145, the first stereo speaker 354, the second stereo speaker 356, the microphone 360, the FM antenna 364, the stereo headphones 366, the RF switch 370, the RF antenna 372, the keypad 374, the mono headset 376, the vibrator 378, and the power supply 380 are external to the on-chip system 322.

According to another particular aspect of the system, one or more of the method steps described herein may be stored in the memory 404A as computer program instructions, such as the modules 120, 125, 130, 135, and 140 described above in connection with the wearable wireless portable device 105A as illustrated in FIG. 1A.

These instructions may be executed by the multicore CPU 402A to perform the method steps described herein. Further, the multicore CPU 402A and memory 404A of the wearable wireless portable device 105A, or a combination thereof may serve as a means for executing one or more of the method steps described herein.

Figure 1C:
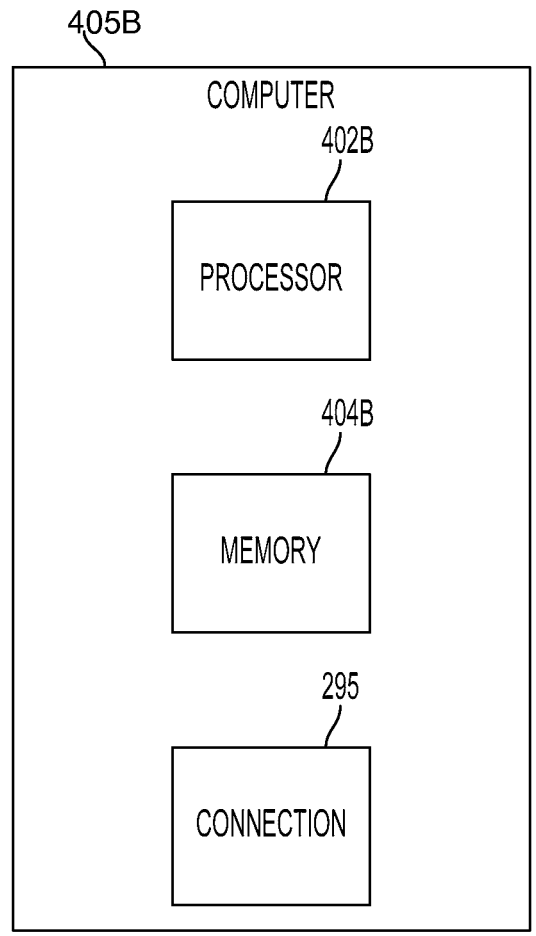
FIG. 1C is a functional block diagram of a general purpose computer that may embody a wearable wireless portable device.

Turning to FIG. 1C, a block diagram of a general purpose computer is illustrated. In one embodiment, the general purpose computer may embody a wearable wireless portable device 105B. The computer may have a processor 402B, a memory 404B, and a connection 295. The processor 402B may be configured by software instructions to perform a variety of methods, including the methods of the various embodiments described herein. For example, the processor 402B may comprise a general purpose processor (e.g., x86, ARM), a digital signal processor ("DSP"), an application specific integrated circuit ("ASIC"), a field programmable gate array ("FPGA"), etc.

The processor 402B may be coupled to and/or execute modules 120-140, which are described above. The modules 120-140 may take the form of software and/or hardware, such as, but not limited to an application integrated circuit ("ASIC"), and/or firmware. These modules 120-140 of FIG. 1A are generally responsible for providing the global positioning functions, bio monitoring functions, exercise/athletic performance tracking functions, personal security functions, and entertainment functions as described above in connection with FIG. 1A.

The memory 404B may be any optical disk storage, any magnetic disk storage, or any other medium operable to store logic and/or data accessible by the computer. The memory 404B may comprise random access memory ("RAM"), read-only memory ("ROM"), electrically erasable programmable read-only memory ("EEPROM"), or any type of solid-state memory that is suitable for compact electronic packaging for a wearable wireless portable device 105.

The connection 295 may generally allow connectivity to other computers, wireless devices, laptops, servers, etc. The connection 295 may comprise a network interface card ("NIC"), a modem, a universal serial bus port ("USB"), a Firewire port, a 3G/4G wireless modem, a near-field communication connection ("NFC"), etc. The connection 295 may be any other wired connection, any other wireless connection, any other magnetic connection, any other visual connection, any other audible connection, etc.

FIG. 2 is a diagram of an exemplary wearable wireless portable exercise 105 with security monitoring and communication functions contained within anatomical mounting hardware 170. In the exemplary embodiment illustrated in FIG. 2, the anatomical mounting hardware 170 comprises a bracelet or ornamental shell suitable for wearing on an arm 255 of a human subject 250. As discussed above, the wearable wireless portable device 105 is not limited to anatomical mounting hardware 170 suitable only for mounting on an arm 255. The mounting hardware 170 may comprise other elements such as a chain or other type of mechanical fasteners such that the wearable wireless portable device 105 may be worn on other regions of the body. For example, the WWPD 105 may take the form as a pendant for wearing around a neck. The WWPD 105 may comprise a unit for attaching to a bicep, or a unit worn on the waist of a human subject 250.

In the exemplary embodiment illustrated in FIG. 2, the display 155A of the wearable wireless portable device 105 may provide numerous pieces of information for the operator such as, but not limited to, the current time of day, and a heart rate 182 of the operator or human subject 250. The display 155A may also show other user interface elements 160A-160G as will be described in further detail below.

The wearable wireless portable device 105 may be coupled to one or more different types of sensors 210. In the exemplary embodiment illustrated in FIG. 2, the sensor 210 may comprise a heart rate sensor. However, other types of sensors are included within the scope of the invention and may include, but are not limited to, breathing sensors, oxygenation sensors, perspiration sensors, blood pressure sensors, glucose meters, temperature sensors, and other like sensors. Other like sensors may measure various different types of physiological parameters that are helpful in monitoring and tracking performance during exercise and athletic activities.

In the exemplary embodiment illustrated in FIG. 2, the heart rate sensor 210 may be supported by a strap 215. Other mounting hardware besides the strap 215 for the sensor 210 may be employed as understood by one of ordinary skill in the art. While the wearable wireless portable device 105 is coupled to the sensor 210 by a wired connection 205, wireless connections (not illustrated) may be used. Wireless connections include, but are not limited to, radiofrequency couplings, magnetic couplings, infrared, and acoustic couplings. Other wireless connections not specifically mentioned are well within the scope of the invention as understood by one of ordinary skill in the art.

The seven user interface elements 160A-160G may be suitable for a display 155A that supports touch-screen type features. This means that for the seven user interface elements 160A-160G, when the operator touches one or more of these user interface elements 160A-160G, then one or more functions and/or features supported by the wearable wireless portable device 105 may become active or accessed by the operator 250.

The first user interface element 160A may comprise an alert button for creating an alert message as described above in connection with FIG. 1A. Such an alert feature may comprise one that allows the operator of the wearable wireless portable device 105A to send an alert status to the server 111. The server may in turn transmit the alert to a remote operator such as a second wearable wireless portable device 105B or a portable computing device 107 as illustrated in FIG. 1A. The portable computing device 107 may be notified to start tracking or monitoring the status of the first wearable wireless portable device 105A.

In other words, the personal security module 135A of the wearable wireless portable device 105 may support an alert feature that does not require immediate action with respect to a party monitoring the location of the wearable wireless portable device 105A. This alert feature, when activated by the first user interface element 160A, may only require the party who has access to the server 111 to start focusing on the location and movement of the wearable wireless portable device 105A. The party may stop monitoring the location and movement of the WWPD 105A when the operator of the WWPD 105A indicates that further monitoring by the third party is no longer needed.

The second user interface element 160B may support an immediate or urgent response feature as described above in connection with FIG. 1A. That is, the second user interface element 160B may support emergency functions and/or features such as a 911 emergency call feature. This means when the 911 function or "Emergency" button feature associated with user interface element 160B is activated, the personal security module 135A may be programmed to send the current location of the wearable wireless portable device 105A. The WWPD 105A may also send a message that may comprise a text message and/or a voice message. The text message and/or voice message may identify the name of the operator of the wearable wireless portable device 105A along with instructions for emergency personnel or first responders to come to the rescue of the operator substantially immediately.

The personal security module 135A as activated by the second user interface element 160B may also support specific emergency functions such as identifying the category or type of emergency. The second user interface element 160B may request emergency assistance corresponding with the category or type selected by the operator of the wearable wireless portable device 105A. This means that the personal security module 135A may support an emergency medical function, an emergency police function, and an emergency fire function, or any combination thereof.

In this way, the operator of the wearable wireless portable device 105A may select the type of emergency that may be experienced by the operator after the second user interface element 160B "Emergency" button is activated. This allows proper emergency personnel or first responders to be appropriately notified and requested to arrive at the location of the wearable wireless portable device 105A.

The third user interface element 160C may support a function in which the operator desires to record and store current exercise or competition/performance data with the wearable wireless portable device 105. The third user interface element 160C may also activate the competition feature described above in connection with FIG. 1A.

The third user interface element 160C may activate the exercise module 130A such that the WWPD 105A receives performance data that is transmitted to the wearable wireless portable device 105A from other wearable wireless portable devices 105B as illustrated in FIG. 1A. Similarly, activation of the third user interface element 160C may also cause the exercise module 130A to transmit the current performance data of the operator 250 of the WWPD 105A over the network 142 to the server 111.

In one exemplary embodiment, activation of the third user interface 160C may initiate the feature in which the wearable wireless portable device 105A receives data regarding other operators of other WWPDs 105B that may be participating in the same exercise or sports activity of the operator 250 of a particular WWPD 105A. Such performance data may include, but is not limited to, geographical locations of other athletes or exercisers that may be shown on display 155, and specific metrics of other athletes such as calories burned, current speed, current exercise or athletic rate, etc. In this way, the wearable wireless portable device 105 may foster competition among multiple athletes and/or exercisers in which these people may be significantly geographically diverse (separate from one another). For example, this may include people comparing performance data to one another who live in different towns, cities, states, countries, etc.

The fourth user interface element 160D may activate a "menu" function that may display various options and/or functions that may be supported by the wearable wireless portable device 105. This fourth user interface element 160D may cause a menu to be shown on the display 155A so the operator 250 may select from the menu elements.

The fifth user interface element 160E may support/activate the "Push-To-Talk" or "Push-To-Transmit" feature described in connection with FIG. 1A above. In one embodiment, activation of the fifth user interface element 160E may initiate QChat®-based instantaneous communications such that the operator 250 may conduct communications using the speaker 150. As noted previously, QChat® is a software application which was developed by Qualcomm, Inc. based in San Diego, Calif. QChat® provides a reliable method of instant connection and two-way communication between users in different locations. QChat® allows users of the wearable wireless portable device 105A to connect instantaneously with other QChat® users anywhere in the world with the push of a button, such as the fifth user interface element 160E.

The sixth and seventh user interface elements 160F, 160G may support conventional chronological features such as the starting and the stopping of a stopwatch such that the operator 250 may track time for an exercise or other form of athletic activity. The six and seven user interface elements 160F, 160G may be coupled to one or more time modules 165 as described above in connection with FIG. 1A.

Figure 3:
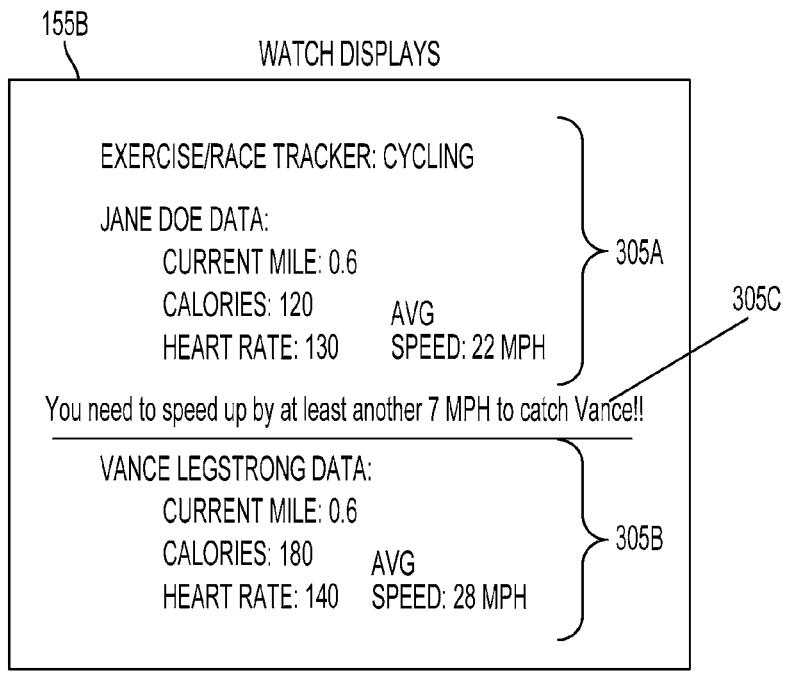
FIG. 3 is a diagram of a screen for displaying exercise data and competition data for an operator of the wearable wireless portable device.

FIG. 3 is a diagram of a screen 155B for displaying exercise data 305A and competition data 305B for an operator of the wearable wireless portable device 105. This screen 155B may be generated by the exercise module 130A which may receive performance data transmitted to the wearable wireless portable device 105A from other wearable wireless portable devices 105B as illustrated in FIG. 1A. In other words, the wearable wireless portable device 105A may receive data, like competition data 305B, related to or associated with other operators of other wearable wireless portable devices 105B. These other WWPDs 105B may be participating in the same exercise or sports activity of the operator of the wearable wireless portable device 105A.

Such performance data may include, but is not limited to, geographical locations of other athletes or exercisers that may be shown on display 155. In one embodiment, specific metrics of other athletes and exercisers such as calories burned, current speed, and current exercise or athletic rate, etc may be shown on the display 155. In this way, the wearable wireless portable device 105 may foster competition among multiple athletes and/or exercisers in which these people may be significantly geographically diverse (separate from one another). This includes people comparing performance data to one another who may live and compete in different towns, cities, states, countries, etc.

In the exemplary embodiment illustrated in FIG. 3, the exercise or athletic activity data 305A of the operator of the wearable wireless portable device 105A may comprise information relating to the activity of bicycling. The athletic data 305A shown on display 155B may comprise information such as but not limited to, distance traversed by the operator during the activity, the amount of calories burned during the activity, the current heart rate of the operator, and the average speed in miles per hour (MPH).

As noted previously, the exercise module 130A may also track and monitor benchmarks associated with stored data such as benchmarks recorded and stored at a server 111 by famous or noteworthy athletes. In one embodiment, the exercise module 130A may provide a continuous comparison of a current exercise or sports activity of the operator of the wearable wireless portable device 105A to stored results of a famous or noteworthy athlete. The famous athlete may have uploaded and stored his or her exercise or sports activity data (also referred to as performance data throughout this document).

In the exemplary embodiment illustrated in FIG. 3, the competition data 305B may comprise benchmarks set by a famous athlete. In this particular example, the famous athlete is in the bicycling field. This competition data 305B may have the same parameters as the athletic activity data 305A. In this particular example, the competition data 305B also includes distance traversed by the athlete at the same location as the operator during the activity, the amount of calories burned during the activity at the same stage for the athlete, the recorded heart rate of the athlete at the same stage of the activity, and the recorded average speed in miles per hour for the athlete at the same stage of activity.

As described above, the competition data 305B may also comprise real-time information of another operator of a wearable wireless portable device 105B. If the operator Jane was racing the operator Vance Legstrong in a live or current activity, then the athletic activity data 305A and competition data 305B would be current, and the parameters for the athletic activity being monitored by the two or more wearable wireless portable devices 105A, 105B would change.

In addition to the exercise data 305A and the competition data 305B, the wearable wireless portable device 105, and specifically, the exercise module 130A may also provide recommendations 305C to the operator so the exercise data 305A may become closer to the competition data 305B or possibly exceed the competition data 305B. For example, if Jane Doe is in a race against the operator Vance Legstrong, then the exercise module may try to help Jane win against Vance. In one embodiment, the exercise module 130A may compare the exercise data 305A to the competition data 305B. The exercise module 130A may also determine that if the operator of the WWPD 105A increases their average speed by at least six miles per hour, then the operator may be able to keep up with their competition in the athletic activity being tracked by the competition data 305B.

Figure 4:
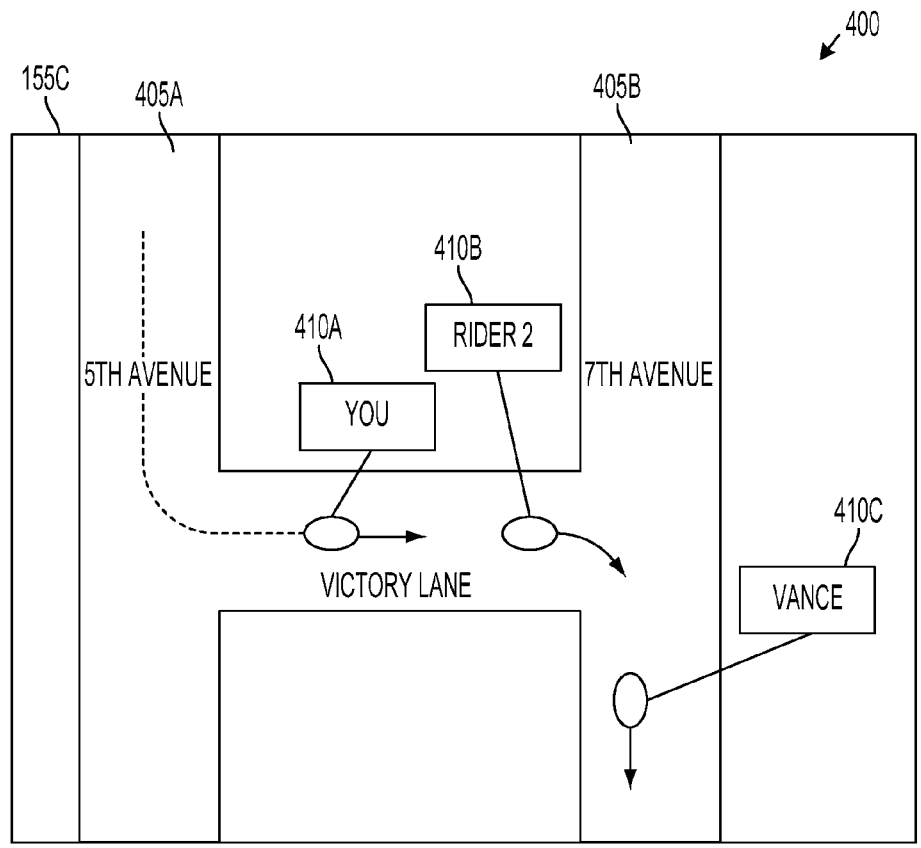
FIG. 4 is a diagram of a screen for displaying a location of the wearable wireless portable device relative to geographical elements and relative to other wearable wireless portable devices.

FIG. 4 is a diagram of a screen 155C for displaying a location 410A of the wearable wireless portable device 105A on a map 400 relative to geographical elements. Geographical elements may include streets 405A, 405B and the screen 155C may show a first WWPD 105A relative to other locations 410B, 410C of second and third WWPDs 105B, 105C. In one embodiment, the maps 400 may be generated by the GPS module 120A in combination with the exercise module 130A.

As noted above, the GPS module 120A may also transmit calculated geographical coordinates of the WWPD 105A over the network 142 to the server 111 using the RF transceiver 115. In this way, a map 400 may be displayed on other devices 105B and 107 that shows real-time geographical coordinates of the WWPD 105A. In map 400, the operator of the wearable wireless portable device 105A is designated by reference character 410A. Meanwhile, other wearable wireless portable devices 105B, 105C have transmitted their respective geographical locations as indicated by reference characters 410B and 410C. These coordinates of the portable devices 105A, 105B, and 105C may be processed and tracked by the exercise module 130A and the GPS module 120A.

The wearable wireless portable devices 105A, 105B, and 105C are represented with oval icons as illustrated in FIG. 4. However, other types of icons that may designate the type of activity being monitored may be used as understood by one of ordinary skill in the art. For example, instead of the ovals used in FIG. 4, bicycle-shaped icons or runner-shaped icons may be used to denote bicycling or running. Other icon shapes and types representative of other activities may be used as understood by one of ordinary skill in the art.

Figure 5:
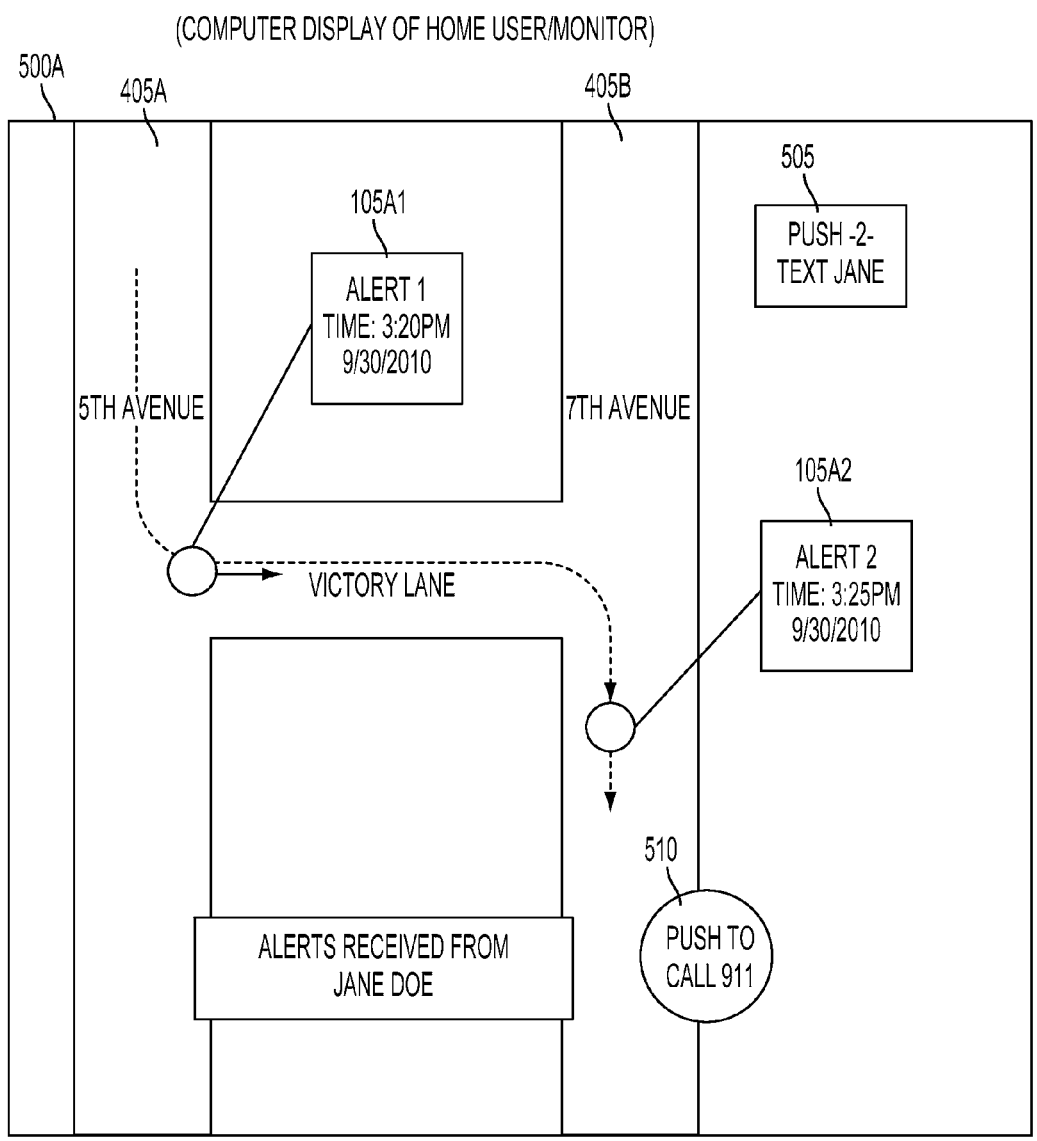
FIG. 5 is a diagram of a screen of a remote portable computing device for displaying a location of the wearable wireless portable device relative to geographical elements such as streets.

FIG. 5 is a diagram of a screen 500A of a remote portable computing device 107 for displaying a location of the wearable wireless portable device 105A relative to geographical elements such as streets 405A, 405B. Screen 500A may be generated based on the coordinates received from a GPS module 120A and information received from the personal security module 135A of wearable wireless portable device 105A.

The portable computing device 107 may comprise a general purpose computer which is coupled to the server 111 via the network 142. Screen 500A may be generated in response to the alert function supported by the personal security module 130A which allows the operator of the wearable wireless portable device 105A to send an alert status to the server 111. These alerts may cause the portable computing device 107 to start tracking or monitoring the status of the first wearable wireless portable device 105A.

In one embodiment, the personal security module 135A may support an alert feature that does not require immediate action with respect to a party monitoring the location of the wearable wireless portable device 105A, such as a party reviewing screen 500A of FIG. 5. This alert feature only may require the party who has access to the server 111 to start focusing on the location and movement of the wearable wireless portable device 105A.

For example, Jane Doe is a bicyclist who decided to generate a first alert 105A1 at time 3:20 pm on Sep. 30, 2010 as illustrated in FIG. 5. Jane activated this alert by pressing the alert button 160A of FIG. 2. After traveling from location designated by the first alert 105A1 in FIG. 5, Jane decided to cancel the alert status by pressing the alert button 160A of FIG. 2 when she reached the second alert location indicated by the second alert 105A2 at 3:25 pm in FIG. 5. Jane decided to cancel the alert since she felt she was riding in a safer area compared to the location of her first alert 105A1 of FIG. 5.

The GPS module 120A of a WWPD 105A may continuously transmit its location to the server 111 such that this continuous movement data may be displayed in screen 500A for the remote portable computing device 107. Screen 500A may support various user interfaces that allow an operator to communicate with the operator of the wearable wireless portable device 105A.

For example, the first user interface element 505 of the screen 500A may comprise a push-to-text feature that allows the operator of the portable computing device 107 to send text or simple messaging service ("SMS") messages to the operator of the wearable wireless portable device 105A. A second user interface element 510 may comprise an on-screen button that allows the operator of the portable computing device 107 to get in contact with first responders such as police, fire, and rescue departments. Other user interface elements may be used as understood by one of ordinary skill in the art.

Figure 6:
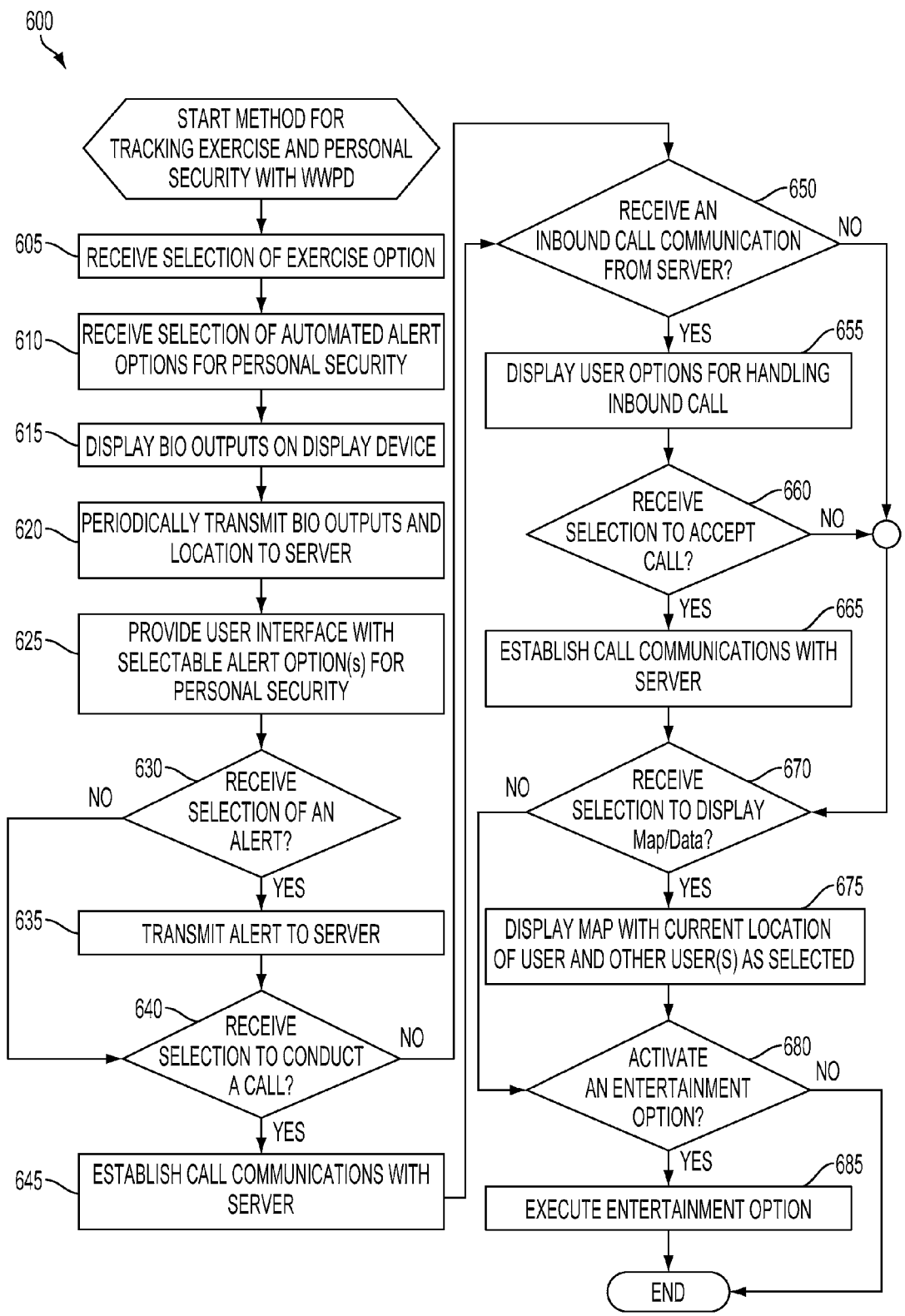
FIG. 6 is a flowchart illustrating a method for tracking exercise and personal security with a wearable wireless portable device.

FIG. 6 is a flowchart illustrating a method 600 for tracking exercise and personal security with a wearable wireless portable communication device. Block 605 is the first step of the method 600 in which the exercise or sports activity module 130A may receive a selection of the type of exercise that an operator of the wearable wireless portable device 105 desires to track. Next, in block 610 the personal security module 135A may receive a selection of one or more options for generating alerts that are transmitted to the server 111 over the network 142. Such options that may be selected include the exemplary first user interface element 160A as illustrated in FIG. 2 in which an operator of the wearable wireless portable device 105 may activate an alert by selecting or touching the "alert button" on the screen display 155A.

Next, in block 615, the biological monitor module 125A and/or the exercise/sports activity module 130A may display one or more biological or physiological outputs on the display device 155A. For example, a heart rate 182 may be displayed on the screen 155A as illustrated in FIG. 2. However, other physiological outputs and/or calculated parameters, like calories burned, etc. may be displayed as options selected by the operator. For example, an operator may decide to select options for displaying heart rate and calories burned simultaneously on the screen 155A.

In block 620, the wearable wireless portable device 105 may periodically transmit the tracked biological or physiological outputs as well as the geographical location of the wearable wireless portable device 105 (as determined by the GPS module 120A) to the server 111. In block 625D, the user interface module 160 may provide user interface elements for personal security such as the first and second user interface elements 160A, 160B as illustrated in FIG. 2.

As described above, the first user interface element 160A may be related to an alert function that may be selectable by the operator of the wearable wireless portable device 105. The second user interface element 160B may support an emergency call function as described above. Other personal security functions that may be tracked by the wearable wireless portable device 105 are included as understood to one of ordinary skill in the art.

In decision block 630, the personal security module 135A may determine if an alert function has been selected by the operator of the wearable wireless portable device 105. If the inquiry to decision block 630 is negative, then the "NO" branch is followed to decision block 640. If the inquiry to decision block 630 is positive, then the "YES" branch is followed to block 635 in which the personal security module 135A may transmit an alert to the server 111 that may be translated into a graphical display such as screen 500A and specifically, the first alert 105A1 as illustrated in FIG. 5.

Next, in decision block 640, the RF transceiver module 115 in combination with the central processing unit 402A may determine if the operator of the wearable wireless portable device 105 desires to conduct a telephone call. If the inquiry to decision block 640 is negative, then the "NO" branch is followed to decision block 650. If the inquiry to decision block 640 is positive, then the "YES" branch is followed to block 645 in which the RF transceiver 115 establishes call communications with the server 111 and or a cellular telephone network 142. Decision block 640 may also correspond with an operator selecting the "Push-to-Talk" feature corresponding to the user interface element 160E as illustrated in FIG. 2.

In decision block 650, the CPU 402A and/or the RF transceiver 115 may determine if the wearable wireless portable device 105 is receiving an inbound call communications from the server 111 or from a cellular communications network 142. If the inquiry to decision block 650 is negative, then the "NO" branch is followed to decision block 670. If the inquiry to decision block 650 is positive, then the "YES" branch is followed to block 655 in which one or more options may be displayed on the display screen 155 to explain how the operator of the wearable wireless portable device 105 may handle a particular call. For example, an operator may elect to take the call and activate the speaker 150. Alternatively, the operator may choose to ignore the call and transfer the call to a voicemail-to-text feature supported by the server 111.

In decision block 660, the CPU 402A may determine if a selection was made by the operator of the wearable wireless portable device 105 to accept the inbound call. If the inquiry to decision block 660 is negative, then the "NO" branch is followed to decision block 670. If the inquiry to decision block 660 is positive, then the "YES" branch is followed to block 665 in which call communications are established with the server 111 and/or a respective cellular telephone communication network 142.

In decision block 670, the GPS module 120A and or the exercise/sports activity module 130A may determine if an operator has selected an option to display a map and/or competition data. If the inquiry to decision block 670 is negative, then the "NO" branch is followed to decision block 680. If the inquiry to decision block 670 is positive, then the "YES" branch is followed to block 675. In this step, map 400 of FIG.

4 may be displayed with a current location of the operator such as location 410A and the locations 410B, 410C of other users.

In decision block 680, the entertainment module 140 may determine if an operator of the wearable wireless portable device 105 has selected an entertainment option. For example, an operator may select playing an audio file like an MP3 type audio file and or a video file in this block. If the inquiry to decision block 680 is negative, then the method 600 ends. If the inquiry to decision block 680 is positive, then the "YES" branch is followed to block 685. In this block 685, the entertainment module 140 may execute one or more of the selected entertainment options, such as playing an audio file, a video file, or a game. The method 600 proceeds to the last block and then ends.

Figure 7:
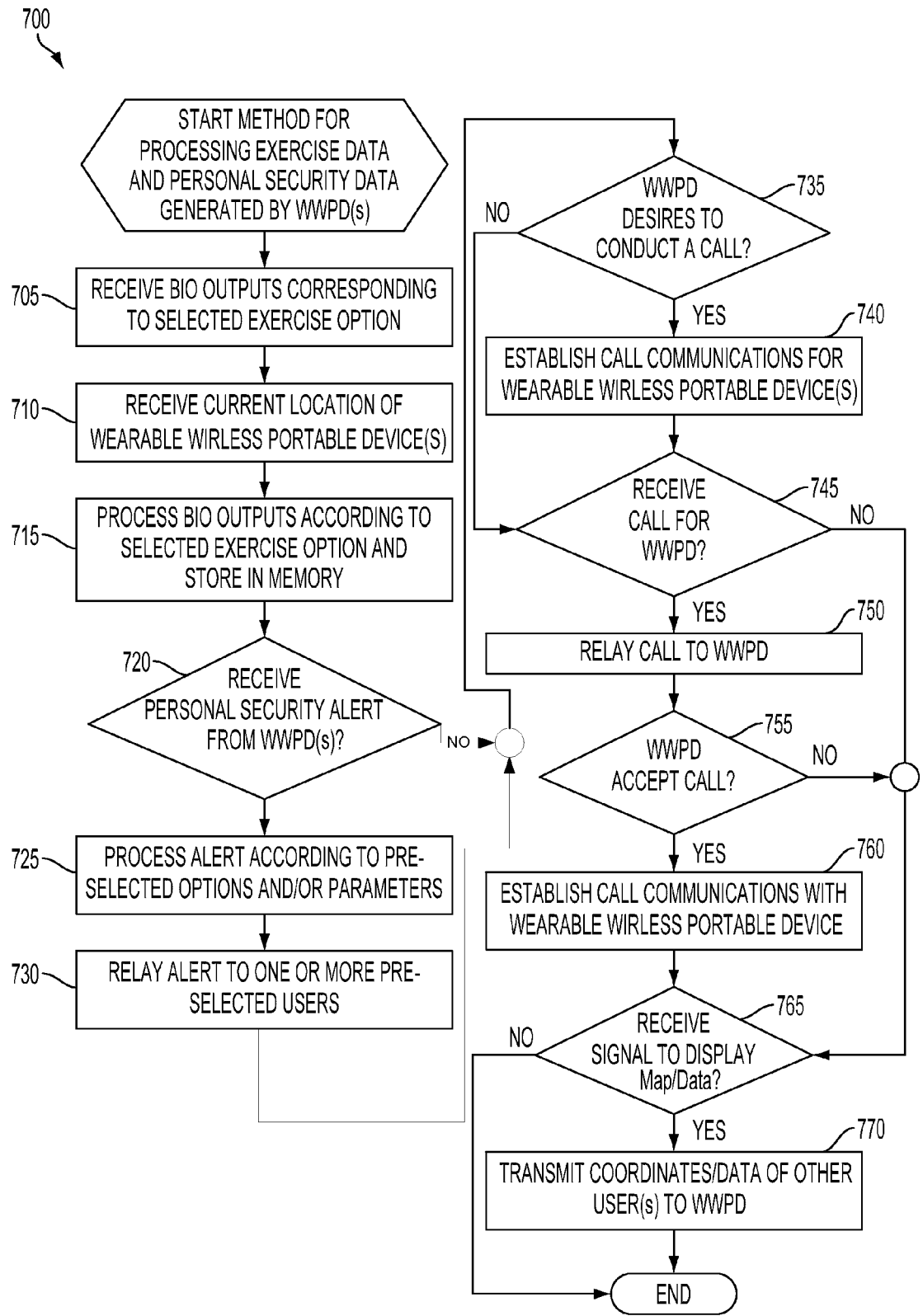
FIG. 7 is a flowchart illustrating a method for processing exercise data and personal security data generated by one or more wearable wireless portable devices.

FIG. 7 is a flowchart illustrating a method 700 for processing exercise data and personal security data generated by one or more wearable wireless portable devices. The first block in the method 700 which is typically executed by the server 111 is block 705. In block 705, the server 111 may receive biological or physiological outputs corresponding to the options selected by the operator of a wearable wireless portable device 105 that are transmitted over the network 142 to the server 111.

Next, in block 710, the server 111 may receive the current location of one or more wearable wireless portable devices 105 that are generated by respective GPS modules 120A. In block 715, the server 111 may process the biological and/or physiological outputs according to the selected exercise option and store these results in memory. For example, the server 111 may track and compare the current biological and or physiological outputs being transmitted over the network 142 to base-line measurements and/or readings in order to determine if there are any problems for the operator of the wearable wireless portable device 105.

Subsequently, in decision block 720, the server may determine 110 if it has received one or more security alerts from one or more wearable wireless portable devices 105. If the inquiry to decision block 720 is negative, then the "NO" branch is followed to decision block 735. If the inquiry to decision block 720 is positive, then the "YES" branch is followed to block 725 in which the server 111 processes the alert according to preselected options and/or perimeters transmitted from the wearable wireless portable device 105A.

In this block 725, the server 111 may generate screen 500A of FIG. 5 and provide the interactive user interface elements 505 and 510 that may be selectable by the operator of the portable computing device 107. In block 730, the server 111 may relay the alert to one or more preselected users such as one or more other wearable wireless portable devices 105B, 105C such as illustrated in FIG. 1A and FIG. 4.

Next, in decision block 735, the server 111 or a cellular telephone network 142 may determine if the operator of the wearable wireless portable device 105 desires to conduct a call. This call may include the "Push-to-Talk" feature described above and/or a conventional cellular telephone network call.

If the inquiry to decision block 735 is negative, then the "NO" branch is followed to decision block 745. If the inquiry to decision block 735 is positive, then the "YES" branch is followed to block 740 in which a call communication for the wearable wireless portable device is established with a cellular telephone network 142 and/or a server 111.

In decision block 745, a server 111 and/or cellular phone network 142 may determine if a call has been received for retransmission to a wearable wireless portable device 105. If the inquiry to decision block 745 is negative, then the "NO" branch is followed to decision block 765. If the inquiry to decision block 745 is positive, then the "YES" branch is followed to block 750 in which the server 111 and/or cellular telephone network 142 relays the phone call to the wearable wireless portable device 105.

In decision block 755, the server 111 and/or cellular phone communication network may determine if the wearable wireless portable device 105 will accept the relayed call. If the inquiry to decision block 755 is negative, then the "NO" branch is followed to decision block 765. If the inquiry to decision block 755 is positive, then the "YES" branch is followed to block 760 in which the server 111 and or cellular-phone communication network 142 establishes the call with the wearable wireless portable device 105.

Next, in decision step 765, the server 111 may determine if the server 111 has received a signal to display a map and or competition data for other wearable wireless portable devices 105. The signal may be generated by the GPS module 120A and/or the exercise/sports activity module 130A of a wearable wireless portable device 105.

If the inquiry to decision step 765 is negative, then the "NO" branch is followed in which the process 700 ends. If the inquiry to decision block 765 is positive, then the "YES" branch is followed to block 770 in which the server 111 may transmit geographical coordinates and/or competition data of other users to the wearable wireless portable device 105. These geographical coordinates may allow the GPS module 120A to generate the screen 155C as illustrated in FIG. 4. The competition data may allow the exercise/sports activity module 130A to produce the screen 155B as illustrated in FIG. 3. The process 700 then ends.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps as understood by one of ordinary skill in the art. In some instances, certain steps may be omitted or not performed as understood by one of ordinary skill in the art. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example.

Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the Figures which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk and blu-ray disc where disks usually reproduce data magnetically, while discs reproduce data optically with lasers. Combinations of the above should also be included within the scope of computer-readable media.

Therefore, although selected aspects have been illustrated and described in detail, it will be understood that various substitutions and alterations may be made therein as understood by one of ordinary skill in the art, as defined by the following claims.

What is claimed is:

1. A method for tracking exercise and personal security using a portable computing device operable to be worn on a person, comprising:
    receiving a selection of an exercise option with the portable computing device;
    displaying a user interface on a display of the portable computing device having a selectable automated alert option for personal security and a selectable instant alert option, wherein the automated alert option is associated with a first alert that does not require immediate attention sent to a party monitoring the portable computing device and the instant alert option is associated with a second alert that requires immediate attention;
    receiving a selection of the automated alert option with the portable computing device;
    displaying one or more biological outputs on the display of the portable computing device and
    supporting two-way audio communications through the portable computing device.

2. The method of claim 1, further comprising displaying a map on the display of the portable computing device.

3. The method of claim 2, wherein displaying the map on the display further comprises displaying a location of other portable computing devices participating in the selected exercise option.

4. The method of claim 1, further comprising displaying competition data associated with another portable computing device participating in a same selected exercise.

5. The method of claim 1, further comprising:
    wirelessly transmitting a location of the portable computing device to a server in a periodic manner in response to receiving the selection of the automated alert option.

6. The method of claim 1, wherein supporting two-way audio communications through the portable computing device comprises supporting a push-to-talk feature.

7. The method of claim 1, wherein the selectable instantaneous alert option comprises an emergency button that provides a wireless signal to a local law enforcement agency, a medical professional, a fire house, or a combination thereof when selected.

8. The method of claim 1, wherein the biological outputs displayed comprise at least one of a heart rate, respiratory rate, glucose level, and calories burned.

9. The method of claim 1, further comprising displaying a current time on the display of the portable computing device.

10. The method of claim 1, wherein the portable computing device comprises one of a bracelet or one or more straps for securing the portable computing device to the person.

11. The method of claim 1, further comprising wirelessly transmitting a location of the portable computing device.

12. A portable computing device for tracking exercise and personal security, comprising:
    a display; and
    a processor connected to the display, wherein the processor is configured with processor executable instructions to perform operations comprising:
        receiving a selection of an exercise option;
        displaying a user interface on the display having a selectable automated alert option for personal security and a selectable instant alert option, wherein the automated alert option is associated with a first alert that does not require immediate attention sent to a party monitoring the portable computing device and the instant alert option is associated with a second alert that requires immediate attention;
        a selection of the automated alert option;
        display one or more biological outputs on the display;
        supporting two-way audio communications through the portable computing device.

13. The device of claim 12, wherein the processor is configured with processor executable instructions to perform operations further comprising:
    displaying a map on the display.

14. The device of claim 13, wherein the processor is configured with processor executable instructions to perform operations further comprising:
    displaying a location of other portable computing devices participating in the selected exercise option on the display.

15. The device of claim 12, wherein the processor is configured with processor executable instructions to perform operations further comprising:
    displaying competition data associated with another portable computing device participating in a same selected exercise on the display.

16. The device of claim 12, wherein the processor is configured with processor executable instructions to perform operations further comprising:
    wirelessly transmitting a location of the portable computing device to a server in a periodic manner in response to receiving the selection of the automated alert option.

17. The device of claim 12, wherein the processor is configured with processor executable instructions such that supporting two-way audio communications through the portable computing device comprises providing a push-to-talk feature.

18. The device of claim 12, wherein the selectable instant alert option comprises an emergency button that provides a wireless signal to a local law enforcement agency, a medical professional, a fire house, or a combination thereof when selected.

19. The device of claim 12, wherein the biological outputs displayed comprise at least one of a heart, respiratory rate, glucose level, and calories burned.

20. The device of claim 12, wherein the processor is configured with processor executable instructions to perform operations further comprising:
    displaying a current time on the display.

21. The device of claim 12, wherein the processor is configured with processor executable instructions to perform operations further comprising:
wirelessly transmitting a location of the portable computing device.

22. A portable computing device for tracking exercise and personal security, comprising:
means for receiving a selection of an exercise option;
means for displaying a user interface having a selectable automated alert option for personal security and a selectable instant alert option, wherein the automated alert option is associated with a first alert that does not require immediate attention sent to a party monitoring the portable computing device and the instant alert option is associated with a second alert that requires immediate attention;
means for receiving a selection of the automated alert option;
means for displaying one or more biological outputs; and
means for supporting two-way audio communications.

23. The device of claim 22, further comprising:
means for displaying a map.

24. The device of claim 23, further comprising:
means for displaying a location of other portable computing devices participating in the selected exercise option.

25. The device of claim 22, further comprising:
means for displaying competition data associated with another portable computing device participating in a same selected exercise.

26. The device of claim 22, wherein
means for wirelessly transmitting a location of the portable computing device to a server in a periodic manner in response to receiving the selection of the automated alert option.

27. The device of claim 22, wherein the means for supporting two-way audio communications through the portable computing device comprises means for supporting a push-to-talk feature.

28. The device of claim 22, wherein the instant alert option comprises an emergency button that provides a wireless signal to a local law enforcement agency, a medical professional, a fire house, or a combination thereof when selected.

29. The device of claim 22, wherein the biological outputs displayed comprise at least one of a heart rate, respiratory rate, glucose level, and calories burned.

30. The device of claim 22, further comprising:
means for displaying a current time.

31. The device of claim 22, further comprising means for securing the portable computing device to a person.

32. A computer program product comprising a non-transitory computer readable storage medium having a computer readable program code stored thereon, said computer readable program code configured to cause a processor of a portable computing device to perform operations comprising:
receiving a selection of an exercise option;
displaying a user interface having a selectable automated alert option for personal security and a selectable instant alert option, wherein the automated alert option is associated with a first alert that does not require immediate attention sent to a party monitoring the portable computing device and the instant alert option is associated with a second alert that requires immediate attention;
receiving a selection of the automated alert option;
displaying one or more biological outputs; and
supporting two-way audio communications through the portable computing device.

33. The computer program product of claim 32, wherein the program code is configured to cause a processor of a portable computing device to perform operations further comprising:
displaying a map.

34. The computer program product of claim 33, wherein the program code is configured to cause a processor of a portable computing device to perform operations further comprising:
displaying a location of other portable computing devices participating in the selected exercise option.

35. The computer program product of claim 32, wherein the program code is configured to cause a processor of a portable computing device to perform operations further comprising:
displaying competition data associated with another portable computing device participating in a same selected exercise.

36. The computer program product of claim 32, wherein the program code is configured to cause a processor of a portable computing device to perform operations further comprising: wirelessly transmitting a location of the portable computing device to a server in a periodic manner in response to receiving a selection of the automated alert option.

37. The computer program product of claim 32, wherein the program code is configured to cause a processor of a portable computing device to perform operations such that supporting two-way communications through the portable computing device comprises supporting a push-to-talk feature.

38. The computer program product of claim 32, wherein the program code is configured to cause a processor of a portable computing device to perform operations such that the instant alert option comprises an emergency button that provides a wireless signal to a local law enforcement agency, a medical professional, a fire house, or a combination thereof when selected.

39. The computer program product of claim 32, wherein the program code is configured to cause a processor of a portable computing device to perform operations such that the biological outputs displayed comprise at least one of a heart rate, respiratory rate, glucose level, and calories burned.

40. The computer program product of claim 32, wherein the program code is configured to cause a processor of a portable computing device to perform operations further comprising:
displaying a current time.

41. The computer program product of claim 32, wherein the program code is configured to cause a processor of a portable computing device to perform operations such that the portable computing device comprises at least one of a mobile telephone, a personal digital assistant, a pager, a smartphone, a navigation device, and a hand-held computer with a wireless connection or link.

* * * * *